United States Patent
Lehmann

(10) Patent No.: US 12,228,558 B2
(45) Date of Patent: Feb. 18, 2025

(54) METHOD FOR ANALYSING WATER

(71) Applicant: Analytik Jena GmbH+Co. KG, Jena (DE)

(72) Inventor: Roland Lehmann, Jena (DE)

(73) Assignee: Analytik Jena GmbH+Co. KG, Jena (DE)

(*) Notice: Subject to any disclaimer, the term of this patent is extended or adjusted under 35 U.S.C. 154(b) by 223 days.

(21) Appl. No.: 17/905,805

(22) PCT Filed: Mar. 8, 2021

(86) PCT No.: PCT/EP2021/055726
§ 371 (c)(1),
(2) Date: Sep. 7, 2022

(87) PCT Pub. No.: WO2021/180620
PCT Pub. Date: Sep. 16, 2021

(65) Prior Publication Data
US 2023/0296578 A1    Sep. 21, 2023

(30) Foreign Application Priority Data
Mar. 9, 2020 (DE) ............... 10 2020 106 340.7

(51) Int. Cl.
| | |
|---|---|
| *G01N 33/18* | (2006.01) |
| *B01D 61/36* | (2006.01) |
| *C02F 1/00* | (2023.01) |
| *G01N 21/31* | (2006.01) |

(52) U.S. Cl.
CPC .......... *G01N 33/18* (2013.01); *B01D 61/364* (2013.01); *B01D 61/366* (2013.01); *C02F 1/001* (2013.01); *G01N 21/31* (2013.01)

(58) Field of Classification Search
None
See application file for complete search history.

(56) References Cited

U.S. PATENT DOCUMENTS

| | | | |
|---|---|---|---|
| 7,479,630 B2 | 1/2009 | Bandura et al. | |
| 2013/0075331 A1* | 3/2013 | Peiris ................ | B01D 61/12 |
| | | | 210/636 |
| 2013/0149790 A1 | 6/2013 | Mennicken et al. | |

(Continued)

FOREIGN PATENT DOCUMENTS

| | | |
|---|---|---|
| CN | 106794409 A | 5/2017 |
| CN | 108698859 A | 9/2018 |

*Primary Examiner* — Suman K Nath
*Assistant Examiner* — Nigel H Plumb
(74) *Attorney, Agent, or Firm* — Christopher R. Powers; Endress+Hauser (USA) Holding, Inc.

(57) ABSTRACT

The present disclosure relates to a method for determining the necessity of an action and/or a success of an action involving water, especially drinking water, process water or waste water, including steps as follows: providing a retentate of a water filter present in a water conveying line, analyzing the retentate regarding at least one property and/or its chemical composition, and determining the necessity or success of the action and, in given cases, deriving the action from the analysis. Furthermore, the present disclosure relates to a system including a means for providing the retentate of a water filter in a water conveying line and a measuring/analytical means for performing the analysis.

21 Claims, 2 Drawing Sheets

(56) References Cited

U.S. PATENT DOCUMENTS

| | | |
|---|---|---|
| 2014/0342397 A1 | 11/2014 | Andersen et al. |
| 2016/0109425 A1 | 4/2016 | Sappok et al. |
| 2016/0340204 A1* | 11/2016 | Chowdhury ............ C02F 1/008 |
| 2019/0039022 A1* | 2/2019 | Kameda ................. B01D 65/02 |
| 2019/0209968 A1* | 7/2019 | Hoz ........................ C02F 1/008 |
| 2020/0064239 A1 | 2/2020 | Bartko et al. |

* cited by examiner

METHOD FOR ANALYSING WATER

CROSS-REFERENCE TO RELATED APPLICATIONS

The present application is related to and claims the priority benefit of German Patent Application No. 10 2020 106 340.7, filed on Mar. 9, 2020, and International Patent Application No. PCT/EP2021/055726, filed Mar. 8, 2021, the entire contents of which are incorporated herein by reference.

TECHNICAL FIELD

The invention relates to a method for determining the necessity of an action and/or a success of an action involving water, especially drinking water, process water or waste water, in a water conveying line. The water can, in such case, be located, for example, in a pipeline or in a container. In the case of a container, the container has a supply line and/or a drain line for filling/emptying the container.

BACKGROUND

For checking the quality of water, numerous methods are known, with which various chemical, physical or microbiological parameters of water samples can be determined. Depending on the investigated property, there occurs either, firstly, a sample taking with following analysis in the laboratory or, in some cases, a field analysis is performed directly on-site.

Especially in the case of drinking water, even slightest contaminants must be detected quickly and reliably. A special problem in this connection comes in the form of bacterial pathogens, for example, *L. Pneumophila* or *P. Aeruginosa*, as well as also in the form of other contaminations of drinking water by nanoparticles and other poisonous substances. Many such contaminations can be detected with usual analytical methods. Often, however, a delay of a number of days is involved, until results are received.

Additionally, required limit values for certain contaminants—in Germany, for example, the drinking water regulation requires a limit value of less than one *E. coli* in 100 ml water—can, with established analytical devices applied for water analysis, not always be regularly obtained. Measuring methods, which are capable of this, such as, for example, continuous PCR measurement, can also be quite expensive and complicated.

Another example of the limits of previous analytical methods concerns ascertaining the TOC value (total organic carbon), which is often too undifferentiated to provide reliable information for the biological quality of water. Prior methods based on biological tests are complicated and often involve days of delays, in order to run a check of drinking water.

Also the increased fouling of the environment with industrially produced nanoparticles is problematic. These get increasingly into the environment and, thus, also into waste water and drinking water, where they are taken up by humans and animals. Nano particles are, exactly as pathogens, quite varied in their structure and composition, upon which their particular pathogenic effects depend. It is, thus, of increasing urgency to register the proportion and composition of small concentrations of particulate substances in water.

A continuous and contemporaneous monitoring of these varied parameters is, currently, not possible, because the available measuring and analytical methods are time consuming and cumbersome, or, in some cases, a reliable analysis is absent.

SUMMARY

Thus, an object of the invention is to provide a method for reliable and comprehensive analysis, or examination, of water, which method is universally applicable and can detect even small amounts of contaminants.

The object is achieved by the method as well as by the system of the present disclosure.

As regards the method of the invention, such is a method for determining the necessity of an action and/or a success of an action involving water, especially drinking water, process water or waste water, and comprises steps as follows:

providing a retentate of a water filter present in a water conveying line, analyzing the retentate regarding at least one property and/or its chemical composition, and determining the necessity or success of the action and, in given cases, deriving the action from the analysis.

The water can be located, for example, in a pipeline, it can, however, likewise be in a reservoir, for example, a container. In such case, the particular containment preferably has a supply line or drain line, in which the water filter can be arranged.

Water filters are often installed in the region of water conveying lines and serve for filtering certain substances from the water and bring about a retention of particles as a function of a filter pore size. Referred to as retentate, or filter cake, in connection with filters is that substance, which is retained in the separation process effected by the filter. The retentate of water filters is usually thrown away. Present concentrated in this retentate, normally, are particulate contaminants (microorganisms, nanoparticles, etc.) of the water. As a result, the retentate is well suited for quantitative and qualitative analysis. Especially contaminants with low concentration in the water can be detected based on the retentate. An examination of the retentate, which is available in large amounts in existing public and private infrastructures, offers, thus, a so far unused, significant information potential.

The invention advantageously enables detection of particulate contaminants present in the retentates comprehensively, locally and near in time. Filter flush water, which contains the retentate and in which the possible contaminants are concentrated, is, currently not used for analysis. Analysis of the retentate represents, thus, a new approach for analysis, with which gaps in the existing water analysis (between waterworks and end-user) can be targetedly eliminated.

In an embodiment of the method, a measuring/analytical means is used for analyzing the retentate, especially a measuring/analytical device for analysis of at least one dissolved and particulate material, preferably a measuring/analytical device in the form of a mass spectrometer, an atomic absorption spectrometer, an atomic emission spectrometer, a Raman spectrometer and/or a hyperspectral microscope, especially in the range of visible light or in the near infrared region. The combination and/or application of different measuring/analytical means assures that different possible contaminants can all be detected. One or more different measuring/analytical means can be applied simultaneously or sequentially for the analyses to be performed. In such case, there occurs targeted selection or combination of different methods, depending on expected information. Mass spectrometry is suited especially for establishing elemental composition, Raman spectroscopy delivers, for example, information on molecular composition of a sample and for phenotypical determination of bacteria. A hyperspectral microscope in the VIS and NIR regions can, in turn, give chemical-structural as well as physical information and also enable a phenotypical determination of bacteria. Using a combination of different detection technologies, a wide range of information concerning the measured particulate contaminants is registered. This information, concerning both elemental and molecular composition of the particles as well as also their structure and shape, enable, taken together, a better identification of the particulate contaminants. It is to be noted here that the measuring/analytical means and their particular capabilities set forth by way of example are not exclusive. Rather, depending on application, for example, depending on the one or more contaminants to be identified, suitable methods can be selected.

Advantageously, the analysis is performed in the single particle or single cell mode. In such an operating mode, instead of a continuous signal, in each case, a short, strong signal from a particular particle or particular cell is received. Examples of devices and methods of these operating modes in spectroscopy are described, for example, in U.S. Pat. No. 7,479,630 B2.

An embodiment of the method of the invention provides that the water filter is a self-cleaning filter. Self-cleaning filters are known per se in the state of the art and are characterized by features including that in high throughput they can filter large volumes of water and can retain particles down to a diameter of 0.2 μm and less. Preferably, the self-cleaning filter is a reversible flow filter or a filter having a suction-scanner For cleaning, the filters are regularly flushed. In such case, the particles previously retained by the filter are released from the filter. Thus, in an advantageous embodiment, the retentate is removed during a cleaning process of the water filter. For example, the flush water used for cleaning the filter and containing the retentate, can be collected from the filter.

By suitable choice of the filter, moreover, the particle size of the retentate contained in the flush water can be suitably selected. This permits, for example, a filtering down to a particle size of 0.2 μm, which lies directly in the size range of bacterial pathogens. By means of a pre-filtering, thus, the final retentate, can, in such case, be limited to a size range of, for example, 0.2 to 10 μm and fed in the flush water to the analysis.

It is, on the one hand, an option to collect retentate in the form of a sample and then to analyze such in a separate measuring/analytical means. Another embodiment of the method provides, however, to convey the retentate from the water filter to a measuring/analytical means for analysis of the retentate. An existing flow system can, for example, be provided with an additional line, through which the retentate, or the retentate containing filter-flush water, is led. The measuring/analytical means can, in such case, be arranged, for example, in the region of the additional line, for example, a bypass line.

Since the contaminants in the retentate are already present concentrated by a filter, the retentate can, in many cases, be directly analyzed without extra preparation steps. It is, however, according to an embodiment of the method, likewise possible that the retentate be earlier cultivated to prepare for the analysis.

Advantageously by means of a mass spectrometric analysis, especially by means of a mass spectrometer with inductively coupled plasma, pathogenic bacteria can be identified and differentiated based on quantitative analysis of their elemental compositions.

An embodiment of the method includes that the water is examined for the presence of a particulate contamination, especially in the form of microorganisms and/or nanoparticles.

Another embodiment includes that the water is examined for the presence, the character and/or the environment of bacteria and/or pathogens, especially a concentration and/or spatial distribution of the bacteria.

Another embodiment provides that a total microbial count in water is ascertained.

Finally, an embodiment of the method includes that the water is examined for the presence of noxa, for example, lead or arsenic.

The examples of different contaminants named here and registrable in the context of method of the invention are, however, not exclusive. Rather, various other properties of water can be examined, depending on the applied measuring and analytical methods.

In an embodiment of the method, the deriving of the action includes at least one of the steps
    starting a cleaning process for decontamination of the water,
    interrupting the supply of water to final consumers, or
    executing at least one extra analysis of the water.

The object of the invention is achieved, furthermore, by a system for determining the necessity of an action and/or a success of an action involving water, comprising a means for providing a retentate of a water filter in a water conveying line; and a measuring/analytical means for examining and/or analyzing the retentate regarding at least one property or its chemical composition.

The system is especially embodied to perform a method of the invention according to at least one of the described embodiments. The water conveying line can be, for example, a pipeline, in which a water filter is located. The water can, however, likewise be located in a standing reservoir, for example, in a container. In such case, the containment advantageously has a supply line or drain line, in which the water filter is arranged. The means for providing the retentate preferably includes at least the water filter, which, in turn, includes especially a filter unit, for example, in the form of a membrane.

In an advantageous embodiment, the system includes means for releasable securement of at least one filter unit of the water filter in the water conveying line. In such case, the retentate can be removed after removing the filter unit from the water conveying line. For example, such can occur upon replacement of the filter unit.

In an additional embodiment, the water filter is a self-cleaning filter, wherein the system includes means for reversing a flow direction of the water through the water filter, for example, a reversing valve, or a cleaning device, for example, a suction scanner. It is likewise advantageous that the system or the water filter include a measuring unit for determining a pressure difference between two regions arranged on opposite sides of the filter. In such case, for example, a cleaning process can be targetedly initiated when the pressure difference exceeds a predeterminable limit value.

The embodiments described in connection with the method of the invention are usable mutatis mutandis also for the system of the invention and vice versa.

BRIEF DESCRIPTION OF THE DRAWINGS

The invention will now be explained in greater detail based on the appended drawing, the figures of which show as follows.

Figure 1:
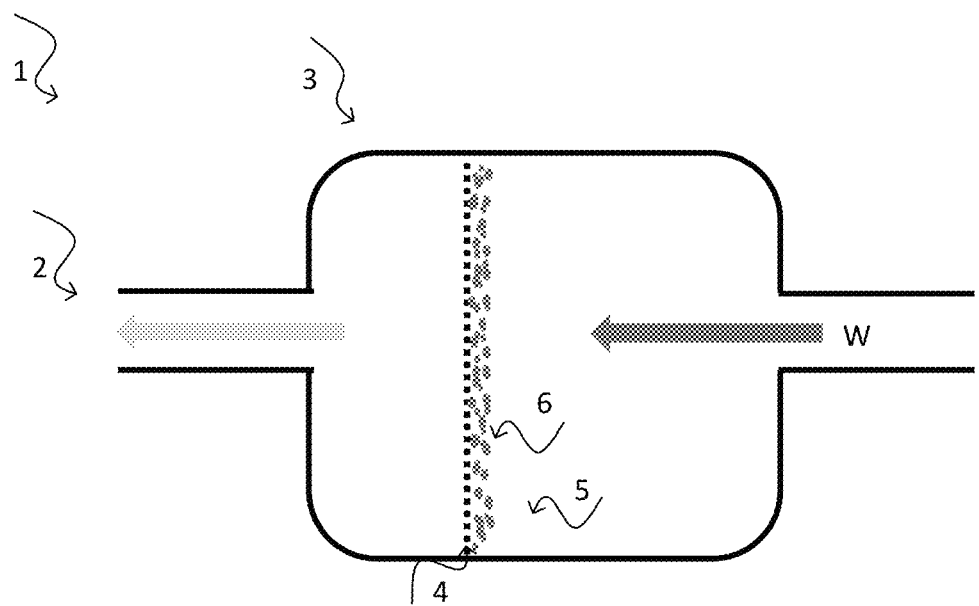
FIG. 1 shows a first embodiment of a system of the present disclosure for determining the necessity of an action and/or a success of an action involving water in a water conveying line having a water filter integrated releasably therein.

In the figures, equal elements are provided with equal reference characters.

DETAILED DESCRIPTION

FIG. 1 shows a first embodiment of a system 1 of the invention. Shown is a pipeline 2 having a means 3 for providing the retentate from the water filter 4, in the case of which a filter unit 5 is integrated releasably into the pipeline 2. The water W flows through the filter 4 in the flow direction indicated by the two arrows. In such case, the retentate 6 collects on the filter unit 5 and is thus held back by the filter 4. Upon removing the filter unit 5 from the pipeline 2, the retentate 6 can be collected and analyzed with a measuring/analytical means 7 (not shown in FIG. 1). In the case of the system 1 shown in FIG. 1, the means 3 and the measuring/analytical means are arranged separately from one another. In other embodiments, the system can, however, be embodied in an even more compact construction, in such a manner that the measuring/analytical means 7 is integrated into the means 3.

Figure 2:
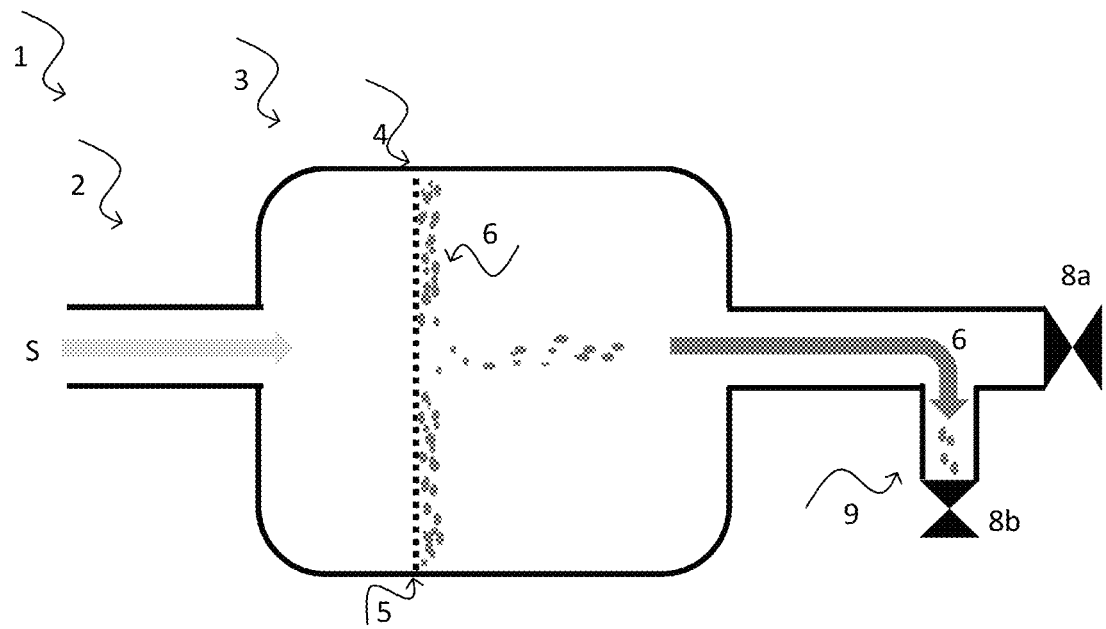
FIG. 2 shows a second embodiment of a system of the present disclosure having a self-cleaning filter with means for reversing the flow direction of the medium through the filter.

In the case of the system 1 shown in FIG. 2, such is equipped with a self-cleaning filter 4 in the form of a reversible flow filter. In normal operation, the pipeline 2 is flowed through by water W similarly to that shown in FIG. 1. FIG. 2 illustrates a cleaning process of the filter 4. The means 3 includes two valves 8a,8b. In the case of the first valve 8a, such is a valve, by means of which the flow direction of the water can be reversed. During the cleaning process, accordingly, flush water S flows through the pipeline 2 in the flow direction indicated by the arrows. During the cleaning process, furthermore, the second valve 8b is opened, such that the flush water S containing the retentate 6 flows into the additional pipeline 9, by which it can be supplied, for example, directly to a measuring/analytical means (not shown in FIG. 2). Either the measuring/analytical means 7 is directly connected to the water conveying line 9, or the retentate 6 containing flush water S can be removed by means of the water conveying line 9 and fed to a measuring/analytical means arranged separately from the means 3.

Figure 3:
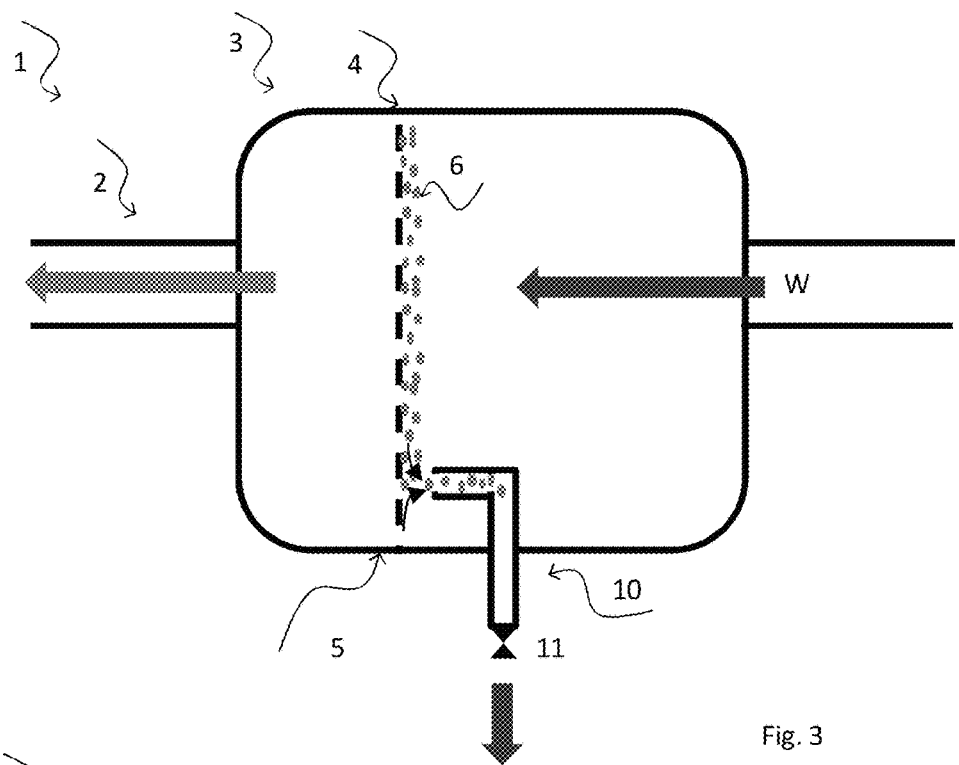
FIG. 3 shows a third embodiment of a system of the present disclosure having a self-cleaning filter and a suction scanner.

Another possible embodiment of a system 1 of the invention with a self-cleaning filter 4 is shown in FIG. 3. In such case, a filter 4 has a suction scanner 10, by means of which the retentate 6 can be removed from the filter unit 5 during a cleaning process. The suction scanner 10 includes a valve 11, via which the retentate 6 can be collected.

Figure 4:
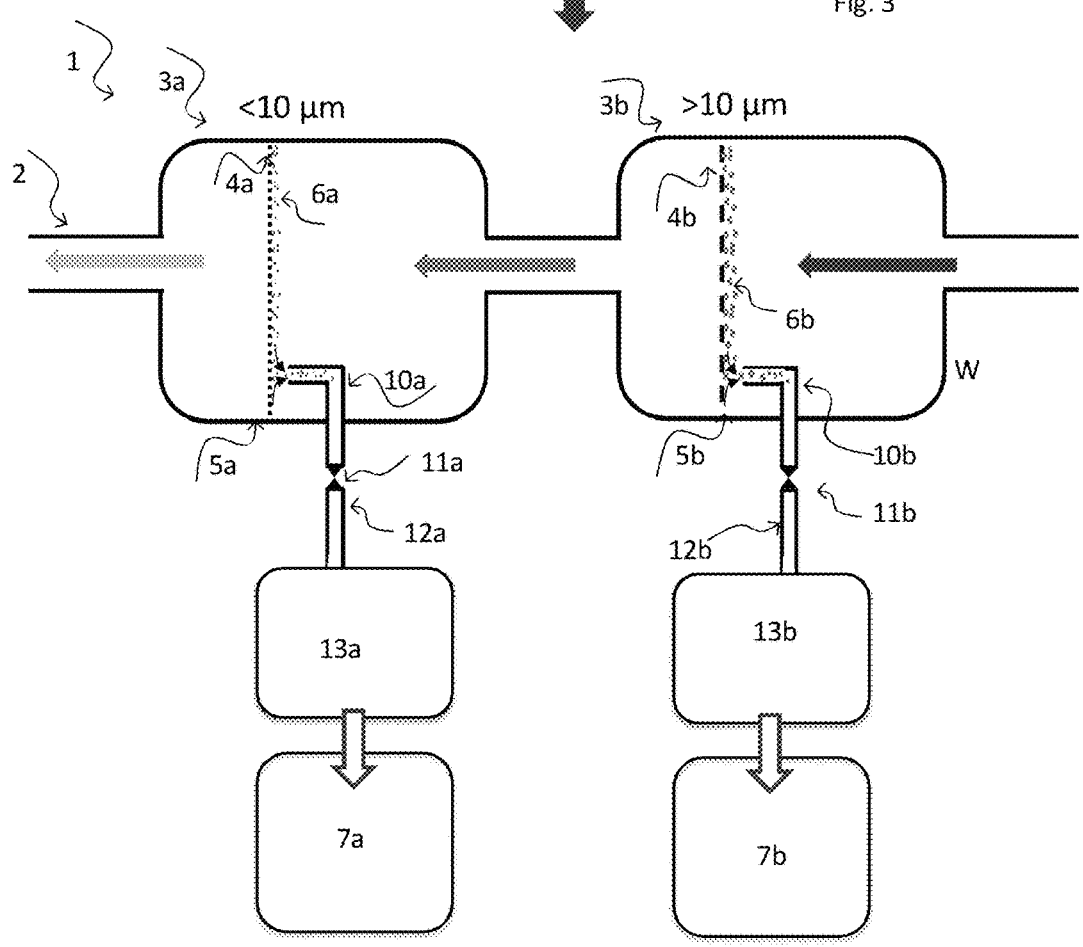
FIG. 4 shows a fourth embodiment of a system of the present disclosure with two water filters and two integrated measuring/analytical means.

A last example of an embodiment of a system 1 of the invention is shown in FIG. 4. The system 1 in such case includes two means 3a,3b for providing retentates 6a,6b using two different filters 4a,4b. The first filter 4a serves for filtering larger particles in water, while the second filter 4b serves for filtering smaller particles. The two filter units 5a,5b have accordingly different pore sizes, wherein the pore size of the first filter unit 5a is greater than the pore size of the second filter unit 5b. In such case, the first filter unit 5a is embodied to filter particles with diameters>10 µm and the second filter unit 5b is embodied to filter particles with diameters<10 µm.

The two filters 4a, 4b are self-cleaning filters, each with a suction scanner 10a, 10b, which, in each case, is connected via a valve 11a,11b and a supply line 12a,12b with a unit 13a,13b for preparing the sample and a measuring/analytical means 7a,7b. The units 13a,13b for sample preparation are optional. For example, these can serve for cultivating samples of retentate 6. The two measuring/analytical means 7 can be equal or different measuring/analytical devices. By suitably choosing the filter units 5a,5b, the retentates 6 can be targetedly influenced, in that the particle sizes are suitably bounded.

In other embodiments, the water W can be located in a standing reservoir (not shown). In such case, the reservoir preferably has a supply/drain line, in which the water filter 4 and means 3 for providing retentate 6 are arranged.

The invention claimed is:

1. A method for determining the necessity of an action and/or a success of an action involving water, the method comprising:
    providing a filter cake from a first water filter and from a second water filter that are disposed in a water conveying line as a retentate, wherein the retentate is provided via at least one suction scanner;
    analyzing the retentate with respect to at least one property and/or chemical composition of the retentate; and
    determining a necessity or a success of an action based on the analysis.

2. The method of claim 1, further comprising deriving the action from the analyzing of the retentate.

3. The method of claim 2, wherein the deriving of the action includes at least one of:
    starting a cleaning process for decontamination of the water;
    interrupting a supply of water to end consumers; or
    performing at least one additional analysis of the water.

4. The method of claim 1, wherein a measuring/analytical means is used for analyzing the retentate, the measuring/analytical means including a measuring/analytical device for analysis of at least one dissolved and particulate material, wherein the measuring/analytical device includes at least one of a mass spectrometer, an atomic absorption spectrometer, an atomic emission spectrometer, a Raman spectrometer and/or a hyperspectral microscope in a range of visible light or in the near infrared region.

5. The method of claim 4, wherein the analysis is performed in a single particle mode or a single cell mode.

6. The method of claim 1, wherein the first and second water filters are self-cleaning filters.

7. The method of claim 1, wherein the retentate is removed during a cleaning operation of the first and second water filters by collecting flush water used for cleaning the first and second water filters and containing the retentate.

8. The method of claim 1, wherein the retentate is conveyed from the first and second water filters to a measuring/analytical means for analysis of the retentate.

9. The method of claim 1, wherein the retentate is cultivated prior to the analyzing preparation for the analysis.

10. The method of claim 1, wherein the water is analyzed for presence of a particulate contamination in the form of microorganisms and/or nanoparticles.

11. The method of claim 1, wherein the water is analyzed for presence, character and/or environment of bacteria and/or pathogens.

12. The method of claim 11, wherein the water is analyzed for a concentration and/or a spatial distribution of bacteria.

13. The method of claim 1, wherein a total microbial count in water is determined.

14. The method of claim 1, wherein the water is examined for the presence of noxa, including lead or arsenic.

15. The method of claim 1, wherein the water is drinking water, process water or wastewater.

16. The system of claim 1, wherein the first water filter is configured to filter larger particles than the second water filter from the water.

17. The system of claim 1, wherein the at least one suction scanner includes a first suction scanner and a second suction scanner, and
    wherein the first suction scanner is configured to remove retentate from the first water filter, and the second suction scanner is configured to remove retentate from the second water filter.

18. A system for determining a necessity of an action and/or a success of the action involving water, the system comprising:
    a first water filter and a second water filter, each disposed in a water conveying line that conveys the water, which includes a contaminant;
    at least one suction scanner operable to remove a retentate from the first water filter and the second water filter in the water conveying line, wherein the retentate is a filter cake of the first water filter and the second water filter, including the contaminate; and
    a measuring/analytical means for examining and/or analyzing the retentate with respect to at least one property or chemical composition of the retentate.

19. The system of claim 18, further comprising a means for reversing a flow direction of the water through the first and second water filters, including a reversing valve or the at least one suction scanner, wherein the first and second water filters are self-cleaning filters.

20. The system of claim 18, wherein the at least one suction scanner includes a first suction scanner and a second suction scanner, and
    wherein the first suction scanner is configured to remove retentate from the first water filter, and the second suction scanner is configured to remove retentate from the second water filter.

21. The system of claim 18, wherein the first water filter is configured to filter larger particles than the second water filter from the water.

\* \* \* \* \*